United States Patent [19]

Renzel et al.

[11] Patent Number: 4,513,621
[45] Date of Patent: Apr. 30, 1985

[54] ULTRASONIC TEST INSTRUMENT WITH CONTROLLABLE AMPLIFIER

[75] Inventors: Peter Renzel, Düren; Klaus Kroesen, Bonn, both of Fed. Rep. of Germany

[73] Assignee: Krautkramer-Branson, Inc., Lewistown, Pa.

[21] Appl. No.: 575,878

[22] Filed: Feb. 1, 1984

[30] Foreign Application Priority Data

Mar. 2, 1983 [DE] Fed. Rep. of Germany ........ 3307224

[51] Int. Cl.³ ............................................. G01N 29/00
[52] U.S. Cl. ........................................ 73/631; 73/611; 73/627; 73/900
[58] Field of Search .................. 73/631, 627, 610, 611, 73/900

[56] References Cited

U.S. PATENT DOCUMENTS

| 4,102,205 | 7/1978 | Pies ........................................ 73/631 |
| 4,398,423 | 8/1983 | Takahashi .............................. 73/631 |
| 4,475,400 | 10/1984 | Flax ........................................ 73/631 |

*Primary Examiner*—Howard A. Birmiel
*Attorney, Agent, or Firm*—E. B. Steinberg; Philip J. Feig

[57] ABSTRACT

The invention relates to an ultrasonic test instrument, in which a receiver amplifier is controlled in dependence upon time by means of a depth compensation signal or else the ultrasonic signal amplified independently of the depth is evaluated by means of a time-dependent variable threshold signal. The depth compensation signals and the time-dependent threshold signals are derived from the same digital signal values stored in a main memory. The test instrument comprises a microprocessor by means of which the digital signal values for each material requiring testing are automatically measured by the instrument itself in conjunction with whichever test probe is used provided a corresponding test block of this material is available. The microprocessor also controls the circuit generating the depth compensation and threshold signals, so that depending upon the type of operation selected the cathode ray tube can display either the ultrasonic·echo responsive signals corrected as a function of depth or the uncorrected ultrasonic signals are shown together with the time-dependent threshold value.

1 Claim, 4 Drawing Figures

ULTRASONIC TEST INSTRUMENT WITH CONTROLLABLE AMPLIFIER

BRIEF SUMMARY OF THE INVENTION

This invention relates to an ultrasonic test instrument for the nondestructive testing of materials having a controllable receiver amplifier and a cathode ray tube for displaying received ultrasonic signals. The receiver amplifier is controlled in response to time by means of a depth compensation signal or, alternatively, the ultrasonic echo signal amplified independently of time is evaluated by means of a time-dependent variable threshold signal. Both the depth compensation signals and the time-dependent threshold signals are derived from a set of digital signal values stored in main memories and converted to corresponding analog values by means of a digital-to-analog converter.

U.S. Pat. No. 4,102,205 of W. Pies et al entitled "Method and Apparatus for Ultrasonic Nondestructive Testing of Workpieces with Automatic Compensation for the Probe, Workpiece Material, and Temperature", dated July 25, 1978 describes an ultrasonic system with various circuits in which the depth compensation signals are obtained by storing in a first memory the DGS (distance, gain, size) values associated with the respective test probe and reading the values out in synchronism with the digital material correction values stored in a second memory, adding those values in an adding stage and then converting the values to corresponding analog values by means of a D/A converter. These analog signals can then be used either as depth compensation signals for the time-dependent control of the receiver amplifier or as time-dependent threshold signals for evaluating the ultrasonic signals amplified without regard to depth.

A specific disadvantage of these prior circuits is that it is not possible to use these circuits for both depth compensation and evaluation of the ultrasonic signals amplified without regard to the depth of the defect. Each individual circuit either provides only depth-dependent control of the receiver amplifier or provides only evaluation of the ultrasonic signals with the time-dependent threshold value. The known circuits fail to contain means for displaying the functional course of the threshold signals, so that it is possible only with difficulty to check these signals. Finally, using the known circuits memories must be provided for both the test probe DGS values and for the material correction values. This requires the use of memories with relative large storage capacity.

One of the objects of this invention is the provision of a test instrument of the type referred to hereinbefore which is adapted to provide depth compensation of the received ultrasonic signals or evaluation of the ultrasonic signals amplified independently of the depth utilizing a time-dependent threshold signal.

Another object of this invention is the provision of a display of the threshold signal true to scale on the screen of a cathode ray tube.

Further and still other objects of this invention will be apparent by reference to the following description when taken in conjunction with the accompanying drawings.

DETAILED DESCRIPTION OF THE INVENTION

Figure 1:
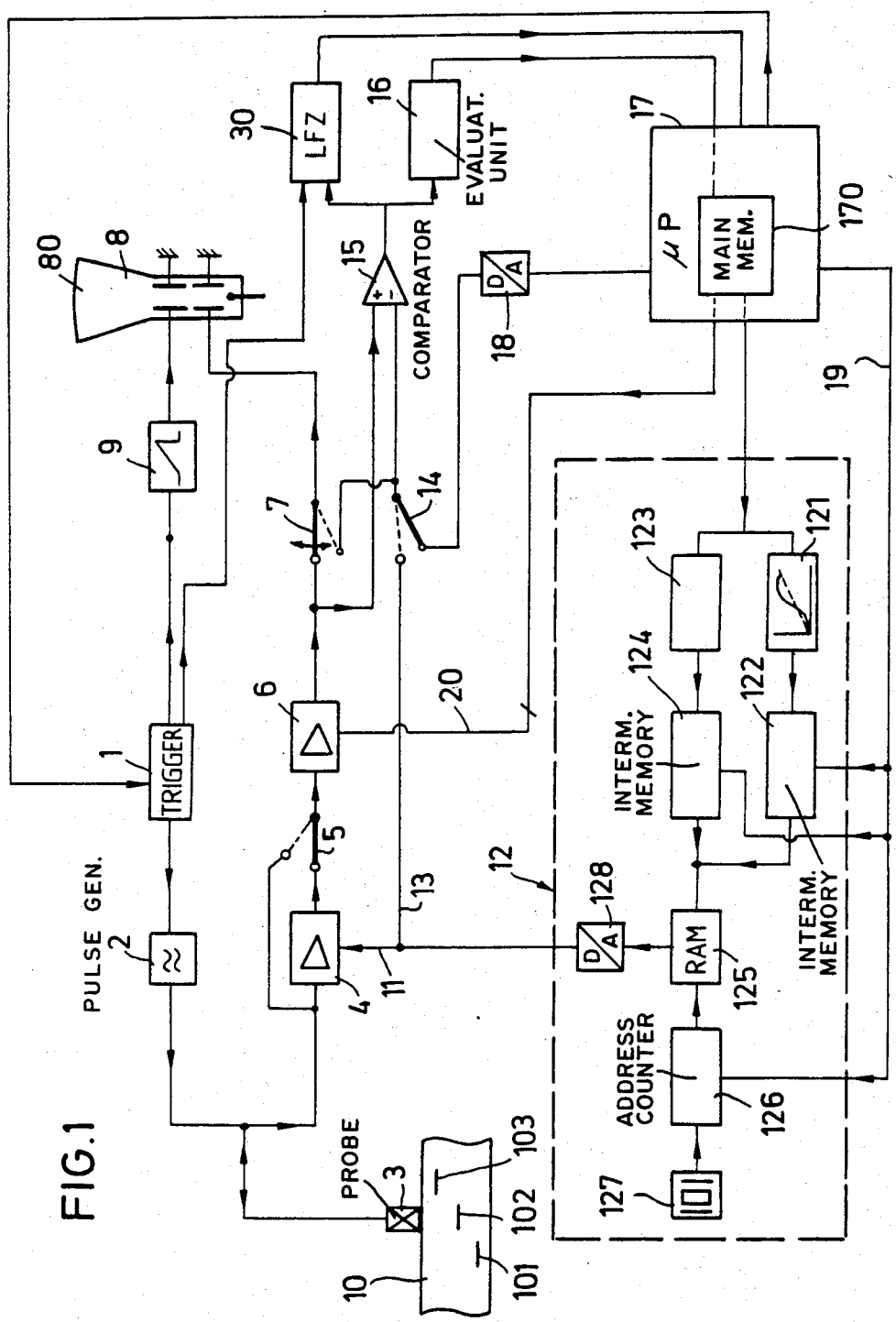
FIG. 1 is a schematic block diagram of the ultrasonic test instrument with circuits according to the present invention.

Referring to FIG. 1, reference numeral 1 denotes a trigger generator which is coupled to a transmission pulse generator 2 which, in turn, is coupled to an ultrasonic test probe 3. A controllable receiver amplifier 4 receives echo signals from the probe 3 and includes also a switch 5 which connects the controllable receiver amplifier 4 to a calibratable amplifier 6. The output of amplifier 6 is connected via switch 7 to the vertical deflection plates of a cathode ray tube 8. The time base for the cathode ray tube 8 is provided in a known manner by a sawtooth generator 9, which is also connected to the trigger generator 1. Test probe 3 is disposed on a calibration test block 10, e.g. made of steel, containing internal flaws 101, 102 and 103 of known size.

The controllable receiver amplifier 4 is connected via conductor 11 to the circuit 12 which is adapted to generate the depth compensation and threshold signals. These signals are fed via a conductor 13 and a switch 14 to one input of a comparator 15, the output of which is connected to an evaluation unit 16 and to a transit time measuring circuit (LFZ) 30. The main memory 170 is a part of a microprocessor 17 in the present embodiment.

The circuit 12 includes a means 121 in which the signal values read out of the main memory 170 are corrected according to the control voltage characteristic of amplifier 4 and then stored in an intermediate memory 122. The values stored in the intermediate memory 122 are the depth compensation signals for controlling the receiver amplifier 4.

The digital signals stored in the main memory 170 are also fed via a unit 123, in which these values are inverted, to the intermediate memory 124. The values stored in this memory are the time-dependent threshold signal values.

The outputs of the two intermediate memories 122 and 124 are connected to a read-write memory (RAM) 125. The contents of this memory can be read out in a known manner by means of an address counter 126, which is controlled by a clock generator 127. The digital values from the memory 125 are converted to corresponding analog values by means of the D/A converter 128.

The microprocessor 17 is used to synchronize the individual memories 122 and 124 and the address counter 126 and trigger 1. This microprocessor can, for example, also deliver a constant threshold voltage, and for this purpose it is connected to comparator 15 via D/A converter 18 and switch 14.

The operation of the ultrasonic test instrument will now be described in detail:

Circuit 12 Used as Depth Compensation Generator

For the condition when the circuit 12 is used as a depth compensation generator, switches 5 and 14 are in the solid line positions shown in FIG. 1. The pulses generated by trigger generator 1 cause the generator 2 to generate a corresponding electrical transmission pulse. This pulse energizes the ultrasonic test probe 3, which in turn generates the corresponding ultrasonic pulse which enters the test block 10 and is reflected by the internal flaw 102. The flaw responsive ultrasonic echo pulse is received by the probe 3, converted to a corresponding electrical pulse, fed to the cathode ray tube 8 via amplifier 4, switch 5, amplifier 6 and switch 7, and is displayed on the screen 80. The timing sawtooth generator 9 is also triggered by trigger generator 1 to obtain the proper time axis position for the echo signal on the screen 80.

A depth compensation signal is fed to the amplifier 4 via conductor 11 in order to provide compensation for the effect of the spatial configuration of the acoustic field of the probe 3 on the measured echo signal amplitudes and the absorption and dispersion characteristic of the test block 10. To this end, before the actual measurement starts, the contents of the intermediate memory 122 are transferred to the memory 125. For accomplishing the depth compensation, the microprocessor 17 activates the address counter 126 so that the contents of the memory 125 are read out synchronized in time with the clock frequency of clock generator 127. The D/A converter 128 causes the digital values to be converted to corresponding analog values, which are then fed to amplifier 4 via conductor 11.

Figure 2:
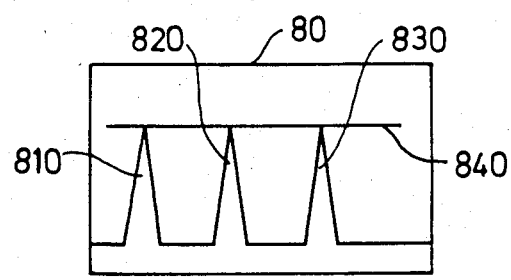
FIG. 2 is a diagram illustrating a rectified A-display produced by the instrument shown in FIG. 1, in which the receiver amplifier is controlled by means of the depth compensation signal.

If the test probe 3 is now moved so that the ultrasonic pulses entering the test block 10 are reflected by the flaws 103 and 101, the cathode ray tube display is as shown in FIG. 2. Pulse 810 on the display screen 80 corresponds to flaw 103, pulse 820 to flaw 102, and pulse 830 to flaw 101. Since the flaws 101, 102 and 103 are of the same size, the echo amplitudes 810, 820 and 830 must all have the same height when a depth compensation signal generator is used.

FIG. 2 also shows a threshold signal 840 for evaluation of the ultrasonic signals, the height of this signal 840 in this case is equal to the height of the three echo signal amplitudes. The height of the threshold signal 840 is set in the mircroprocessor 17. The signal passes via the D/A converter 18 and switches 14 and 7 to the cathode ray tube 8. To display both the ultrasonic signals and the threshold voltage, switch 7 switches back and forth between the amplifier 6 and switch 14 at a speed such that the viewer sees the two signal voltages practically simultaneously on the display 80. The threshold voltage is additionally fed to the comparator 15 for evaluation of the ultrasonic signals in circuit 16 and for measurement of the transit time in circuit 30.

Circuit 12 Used as Threshold Generator

If the circuit 12 is to be used as a threshold generator, the switches 5 and 14 are switched to the positions shown by the dashed lines. Microprocessor 17 now activates intermediate memory 124 so that the corresponding stored values are transferred to the memory 125 and the previously stored depth compensation values are erased. To evaluate the received ultrasonic echo signals, the threshold values are read out in synchronism with the clock frequency of the clock generator 127 from the memory 125 and fed via D/A converter 128, and via conductors 11 and 13 and switch 14, both to the comparator 15 and, via switch 7, to the cathode ray tube 8. The ultrasonic echo signals are amplified only in the calibratable amplifier 6 and displayed directly on the screen 80 of the cathode ray tube 8. Switch 7, in turn, switches back and forth between the amplifier 6 and switch 14.

Figure 3:
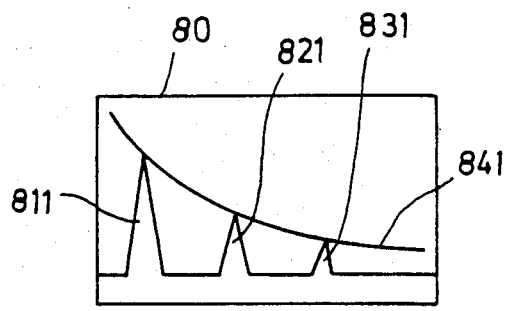
FIG. 3 is a diagram showing a rectified A-display produced by the instrument shown in FIG. 1, in which the ultrasonic signal amplified independently of the depth is evaluated by means of a threshold signal which is variable as a function of time.

FIG. 3 shows the corresponding display. Echo signal 811 corresponds to the flaw 103, echo signal 821 to flaw 102 and echo signal 831 to flaw 101. The threshold voltage is denoted by reference numeral 841. The height of the echo amplitudes 811, 821 and 831 decreases due to the increasing depth of the reflectors 103, 102 and 101. The peak values of the individual echo amplitudes just touch the time-responsive threshold voltage.

Determination of Signal Values Stored in Main Memory, and of Depth Compensation and Threshold Values A particular advantage of this invention is that both the depth compensation values and the threshold values can be derived from the same digital signal values contained in a single main memory. These digital signal values are automatically determined by means of the same ultrasonic test instrument which subsequently is used to carry out the depth compensation and threshold comparison.

The first step in determining the stated signal values, for example using the control object 10 shown in FIG. 1, is to determine in decibels by means of the calibratable amplifier 6 the amplification values required for the echo signals responsive to flaws 101 to 103 (usually at least ten test flaws of different depths are used) to be amplified to a constant height, e.g. 80% of the screen.

The amplification of the calibratable amplifier 6 is adjusted by means of digital adjusting signals fed by microprocessor 17 to amplifier 6 via conductor 20. Each digital adjustment value corresponds to a specific gain of the amplifier 6. If the amplitude of the amplified ultrasonic signals reaches the threshold voltage at comparator 15 (which in this example corresponds to a threshold signal 840, FIG. 2, equal to 80% of the screen height), the feeding of increased digital adjustment values is stopped and the last supplied adjustment value is stored directly as a signal value in the memory 170.

The transit time of the corresponding ultrasonic pulse to the reflectors 101 to 103 as determined by the transit time unit 30 is used as an address for the respective memory locations.

Intermediate values, i.e. signal values corresponding to reflectors situated intermediate the calibrated reflectors 101 to 103 are determined, for example, mathematically by linear interpolation from the measured signal values and stored in the main memory 170.

Figure 4:
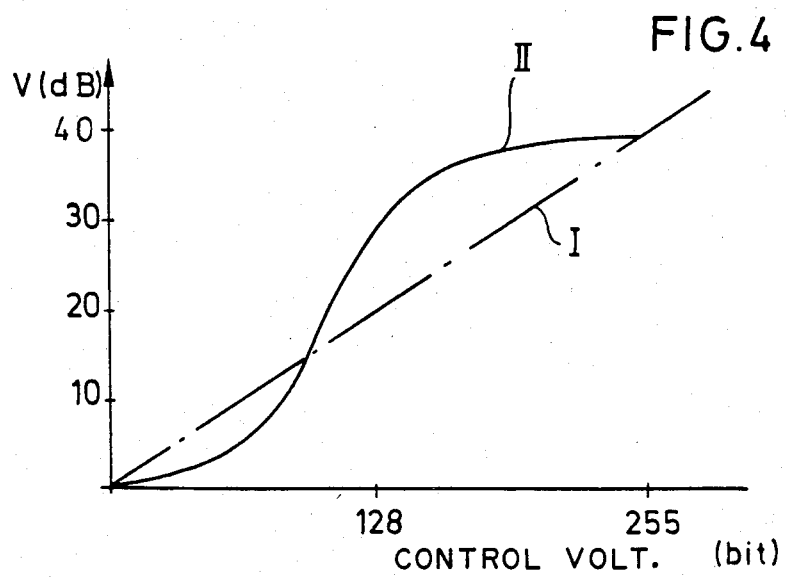
FIG. 4 is a graph showing the control voltage characteristic of the controllable receiver amplifier used in FIG. 1.

Of course, the signal values stored in this way cannot be used directly as depth compensation values. Rather, they have to be corrected according to the control voltage characteristic of the controllable amplifier 4. FIG. 4 depicts an example of the control voltage characteristic of this kind for a commercially available amplifier. The vertical axis shows the gain of the amplifier 4 in decibels and the horizontal axis shows the control voltage in digital units.

If there were a linear relationship between the gain and the control voltage (curve I), the values stored in the main memory could be used directly (after standardization to a reference value) as depth compensation values. In practice, however, the control voltage characteristic is as shown by curve II in FIG. 4. The values stored in the main memory must therefore be corrected in accordance with the actual control voltage characteristic. This can be done, for example, by means of a separate unit 121. A unit of this kind consists basically of a fixed value memory in which the control voltage correction values correpsonding to the amplifier 4 are stored and then added, via an adding stage, to the values stored in the main memory.

Advantageously, however, when a microprocessor 17 is used, the amplification values stored in the main memory are converted to the depth compensation values by means of a conversion table stored in the processor and these values are then stored in the intermediate memory 122. This conversion table can also be determined by means of the ultrasonic test instrument shown in FIG. 1. To this end, for example, test probe 3 is set to the position shown in FIG. 1, so that only signal 821 (FIG. 3) appears on the screen 80. The gain of the controllable amplifier 4 is then set to zero decibels (0 db) and the gain of the calibratable amplifier is raised until the peak of the signal 821 reaches 80% of the screen height for example. The amplification of amplifier 6 is then reduced by one db by means of a corresponding digital adjustment value signal fed to amplifier 6 by microprocessor 17 via conductor 20. The control voltage of the amplifier 4 is then increased until the peak of the echo signal 821 again reaches 80% of the screen height.

The corresponding digital voltage values (both the digital adjustment signal on conductor 20 and the digital control voltage value (in bits) for controlling the amplifier 4), are then stored in a table memory, which may be part of the main memory 170. The amplification of amplifier 6 is then reduced by another decibel and the gain of the amplifier 4 is raised again until the echo signal 821 reaches 80% of the screen height. The entire balancing operation is continued until the gain of the calibratable amplifier 6 is zero decibels.

Logarithmic amplification values stored in the main memory 170 are utilized to generate the threshold values. These values are delogarithmized and converted to inverse function values by means of a unit 123. This is again done, for example, by means of microprocessor 17, in which each amplification value Va is converted by the following equation to a corresponding threshold value Sa:

$$Sa = 10^{(Vo-Va)/20} * 80\%$$

where Vo denotes the lowest reference amplification value stored in memory 120. These values, calculated in this manner are then transferred to the intermediate memory 124.

While there has been described and illustrated a preferred embodiment of this invention, it will be apparent to those skilled in the art that certain changes and modifications can be made therein without deviating from the spirit of the invention which shall be limited only to the scope of the appended claims.

What is claimed is:

1. An ultrasonic test instrument for nondestructive testing of materials having a controllable receiver amplifier and a cathode ray tube for displaying the received ultrasonic echo signals, in which the receiver amplifier is controlled in dependence upon time by means of a depth compensation signal, or else the ultrasonic echo signal amplified independently of time is evaluated by means of a time-dependent variable threshold signal, and in which both the depth compensation signals and the time-dependent threshold signals are derived from digital signal values stored in main memories and converted to corresponding analog values by means of a digital-to-analog converter, the improvement comprising:

a single main memory;

a first and a second intermediate memory coupled in series with said main memory, said first intermediate memory containing signal values corrected with respect to the signal values stored in said main memory taking into account the control voltage characteristic of the receiver amplifier, and said second intermediate memory containing inverse voltage signal values with respect to the signal values stored in the main memory;

a read-write memory coupled with its input to said first and said second intermediate memory;

the output of said read-write memory connected via said digital-to-analog converter to the controllable receiver amplifier and for displaying the threshold signal connected also via switches to said cathode ray tube, and said controllable receiver amplifier coupled in series with a calibratable amplifier calibrated in decibels for determining the digital signal values stored in said main memory.

* * * * *